(12) United States Patent
Utsugi (10) Patent No.: US 6,502,583 B1
(45) Date of Patent: Jan. 7, 2003

(54) METHOD OF CORRECTING FACE IMAGE, MAKEUP SIMULATION METHOD, MAKEUP METHOD MAKEUP SUPPORTING DEVICE AND FOUNDATION TRANSFER FILM

(75) Inventor: Ryuichi Utsugi, Tokyo (JP)

(73) Assignees: DRDC Limited, Tokyo (JP); Scalar Corporation, Tokyo (JP)

( * ) Notice: Subject to any disclaimer, the term of this patent is extended or adjusted under 35 U.S.C. 154(b) by 0 days.

(21) Appl. No.: 09/380,406
(22) PCT Filed: Mar. 6, 1998
(86) PCT No.: PCT/JP98/00943
§ 371 (c)(1),
(2), (4) Date: Sep. 1, 1999
(87) PCT Pub. No.: WO98/39735
PCT Pub. Date: Sep. 11, 1998

(30) Foreign Application Priority Data

Mar. 6, 1997 (JP) ............................................... 9-051460

(51) Int. Cl.[7] ........................ A45D 24/00; G09B 23/28; G06K 9/00
(52) U.S. Cl. ........................ 132/200; 434/262; 382/128
(58) Field of Search ........................ 132/200; 434/262, 434/100, 98, 81; 382/128, 294, 130, 151; 364/400, 413.01, 479.02

(56) References Cited

U.S. PATENT DOCUMENTS 5,785,960 A  *  7/1998  Rigg et al. ..................... 424/63
5,854,850 A  * 12/1998  Linford et al. .............. 382/128
6,293,284 B1 *  9/2001  Rigg et al. ................... 132/200

FOREIGN PATENT DOCUMENTS

WO          WO92/02000          2/1992

* cited by examiner

*Primary Examiner*—John J. Wilson
*Assistant Examiner*—Robyn Kieu Doan
(74) *Attorney, Agent, or Firm*—Michael D. Bednarek; Shaw Pittman LLP (57) ABSTRACT

New findings such as the highlight theory which determines the impression of a face are utilized for the technology of correcting the photograph of face image and for the makeup technology. The method includes determining a requested face which is requested by the person who wants the photograph to be corrected or wants to be made up, and creating an image of the face corrected or made up by executing image-processings such as contour—combining of the original face image or the face of the person based on the requested face.

15 Claims, 5 Drawing Sheets

METHOD OF CORRECTING FACE IMAGE, MAKEUP SIMULATION METHOD, MAKEUP METHOD MAKEUP SUPPORTING DEVICE AND FOUNDATION TRANSFER FILM

TECHNICAL FIELD

The present invention relates to a technique of modifying facial images and a makeup art of putting makeup on a face using the modifying technique.

BACKGROUND OF THE INVENTION

The present inventor has been making studies, for a long time, on factors which determine the faces of persons, particularly facial impressions, and beauty and ugliness, from the viewpoints of plastic surgery and cosmetic surgery. The study has provided several new findings. One of them is the "highlight theory". Conventionally, it was a general thought that the components of a face, such as eyebrows, eyes, a nose and lips, would become significant factors to determine a facial impression. The research done by the present inventor however shows that the prime factor to determine a facial impression is the shading state of a face, i.e., the states of a bright area and a dark area, particularly, the state of the brightest area or highlighted area. The shading state relates to shading on a face which occurs under illumination of the natural light, and reflects or expresses the three-dimensional shape of the face. The states of a highlighted area in such shading particularly affects a facial impression.

The analysis based on this highlight theory classifies faces into three general types. As exemplarily shown in FIG. 5, the shapes of highlighted areas are an inverted triangle type [(a) in FIG. 5], an oval type [(b) in FIG. 5] and a clover-leaf type [(c) in FIG. 5]. A typical beautiful face in each facial type has a good shape of the associated highlighted area. With regard to an inverted triangle type, for example, no or little distortion or deformation on its shape is a significant factor in giving a good impression on a face.

Another finding is a theory on the shapes of faces people feel beautiful or preferable. Conventional theories on facial beauty include canon theory or a theory based on golden cut, and the average theory which has recently come up. The average theory means a theory that the face that appears most beautiful among those of a certain human race is an average face of the individual faces of that race. Faces based on those theories merely provide general "beautiful faces". In other words, those theories cannot give ideal post-makeup faces which are makeup aims applicable to makeup methods. Unlike those theories, the theory found by the present inventor can be put to a practical use in makeup methods.

According to what has been newly found by the present inventor, through the following procedures, it is possible in most occasions to find the most beautiful or preferable face for each specific person, or the most beautiful or preferable face that can be made by makeup available to that individual. The fundamental theory is such that if faces are produced by combining a face of given standards, specifically, a face generally considered beautiful or a face preferred by an individual and the actual face of that particular individual at the proper mixing ratios through an image processing technique, an "ideal face" which is considered most beautiful or preferable by that individual can be found in most cases from the foregoing mixed faces. Specifically, one of model faces, which are, for example, faces of preferred talents or actresses or actors, or "beautiful faces" originated from the average theory and the like, is selected as a desirable face. Based on this desirable face, the actual face of the person is subjected to image processing like morphing so that the actual face is mixed with the desirable face to approach the latter. This process provides a plurality of "modified faces" with different mixing ratios or similarity levels with respect to the desirable face. In most cases, those "modified faces" contain an "ideal face" that person considers most beautiful or preferable. The data obtained by the present inventor shows that persons in 48 cases out of 50 could find "ideal faces" they thought most beautiful or preferable. In the other two cases, "ideal faces" could be found by modifying the desirable faces. The mixing ratio in every case ranged from 10 to 50%.

It is to be noted that one model face itself should not necessarily be the most preferable face for a particular person. That is, the "ideal face" a particular person can find for herself or himself is a "modified face" which is resulted from the mixing of a model face with her or his own face, not the model face itself. The actual results of the experiments conducted by the present inventor show that most subject persons did not prefer model faces using "beautiful faces" created by the average theory or the like.

The present invention has been devised to effectively utilize the above-described findings and alms at using those findings to a technique of modifying, for example, photographed facial images and to a makeup technique.

DISCLOSURE OF THE INVENTION

According to the present invention, facial images picked up by a still camera, a video camera or the like are modified as follows. First, a desirable face is determined, and then an original facial image is subjected to image processing to become closer to this desirable face so that a modified facial image is acquired.

Model faces can be used in determining a desirable face. The faces of preferable talents or actresses or actors can be used as model faces. If one does not have any preferable talent or the like, standard good-looking faces acquired from a plurality of beautiful faces which have previously been prepared corresponding to human races or like according to the foregoing average theory may be used. In the foregoing method, it may also be arranged that an original facial image is subjected to image processing to become closer to a desirable face, thereby forming images of a plurality of selectable modified faces with different similarity levels with respect to the desirable face, and then a selection is made from those selectable modified faces to acquire a modified facial image. This further facilitates acquiring a face ideal to the subject person.

It is preferable to use the foregoing highlight theory in modifying and making an original facial image closer to a desirable face. That is, the key point is to make the states of highlighted areas of a facial image to be modified closer to those of a desirable face. This can provide a more beautiful and preferable face and thus facilitate approaching to a desirable face.

This facial image modifying method is an application of the foregoing theory on the shapes of faces that people think beautiful or preferable. Unlike the conventional photograph modification techniques which mainly depend on a manual work, this method can automate the modification work by electronic processing. What is more, modification results can give greater satisfaction. This method of the present invention can be adapted to operational simulation in plastic surgery and cosmetic surgery as well as ordinary photograph modification.

In a makeup simulation method embodying the present invention and a makeup method which uses this simulation method, a desirable face is determined first. In the case where a makeup instructor instructs a subject person how to put makeup, for example, a desirable face may be determined by asking the subject person about preferences. Alternatively, model faces may be used in determining a desirable face. The faces of talents, or actresses or actors the subject person like can be used as model faces. If the subject person has no preference for any talent or the like, averages of good-looking faces which have previously been prepared corresponding to human races or the like may be used as model faces. In the former case, a preferred desirable face can be selected from model faces using the name or the like of the preferable talent or the like as an index. In the latter case, a preferred desirable face should be selected from model faces of standard beauty which has previously been input as data. In both cases a selection is made while sequentially displaying the model faces on a monitor screen or based on the type of the face of the subject person. In the latter case, the model faces should not necessarily be shown to the subject person.

Once the desirable face is decided, then images of imagined post-makeup faces based on the desirable face or post-makeup faces which are imagined as preferable are prepared. This involves a process of mixing the face of the subject person with the desirable face to make the former face closer to the latter by performing image processing like shape-merging on the image of the face of the subject person. Then, an ideal post-makeup face the subject person desires is determined from the imagined post-makeup faces. Specifically, a plurality of imagined post-makeup faces with different mixing ratios or similarity levels with respect to the desirable face are acquired through the foregoing image processing, and a preferable selection is made from those faces as an ideal post-makeup face within the range of the similarity levels which can be obtained by makeup. Thus, the ideal post-makeup face which is expected to be finally obtained is given in advance. That is, the subject person can know the makeup-finished face in a short time. As apparent from the above, the significant feature of the makeup method embodying the present Invention lies in that a final, makeup-finished face can be presented in a short time by determining a desirable face on which a makeup procedure is based and acquiring an ideal post-makeup face with respect to this desirable face. In this feature is effectively used the above-described theory on the shapes of faces people think beautiful or preferable.

When an ideal post-makeup face is decided through the foregoing makeup simulation, a makeup procedure is derived from this ideal post-makeup face. Specifically, a sequence of makeup procedures for achieving the ideal post-makeup face, such as selecting which portions of eyebrows to be shaved and where to draw eyebrows, selecting the lines and ranges for eye liners and eye shadows, selecting the colors of eye shadows, setting the drawing range for a lipstick and separately applying different foundations, is derived from a previously set makeup program. Based on this makeup procedure, makeup is applied to the subject person. This makes it possible to accurately realize the ideal post-makeup face or the makeup state the subject person has previously found appropriate, on the face of the subject person. That is, makeup which the subject person desires can be done freely and in a short time.

To realize the foregoing feature of the makeup method of the present invention which lies in the preparation of an ideal post-makeup face through image processing based on a desirable face or a model face, it is important to mix the current face of a subject person with a model face through image processing to get the former face closer to the latter. That is, it is essential to acquire an ideal post-makeup face by making the current face of the subject person closer to the reference model face by image processing. The feature also requires an effective scheme or standards for making the current face of the subject person closer to the ideal post-makeup face by actual makeup. This can be accomplished by the foregoing highlight theory.

Based on the highlight theory which teaches highlighted areas considerably affect the impression of a face and a beautiful and preferable face can be made by erasing any unnecessary shade (dark area) to make the shapes of the highlighted areas better, it becomes relatively easy to get the face of a subject person closer to a model face through image processing and it is also easy to make the face of the subject person closer to a desirable face by implementing such a makeup as to adjust the states of the highlighted areas in association with those of the model face (desirable face). In other words, a more effective scheme of making the face of the subject person closer to the reference model face can be acquired based on the highlight theory.

The image processing for preparing the images of imagined post-makeup faces on the basis of the highlight theory involves a process of making the shapes of the eyebrows, the eye lines, the lip line, and so forth closer to those of a desirable face within a range where modification by makeup is possible, in addition to the basic process of getting the states of highlighted areas on a face closer to those of the desirable face within a range where modification by makeup is possible. A shape-merging scheme or the like can be also used in this case.

Based on the highlight theory, attention should be paid to a greatest highlighted area as an impressing element of a face in the makeup simulation method and makeup method, too. Since makeup about highlighted areas is accomplished by separately applying different foundations, the types of foundations and procedures for applying them separately are derived as essential factors from an ideal post-makeup face.

To accomplish the process, image processing is performed to divide the ideal post-makeup face into a plurality of areas originating from differences between bright and dark areas like a pattern of contour lines. Then, color data is acquired for each segmented area. Color data in this case consists of hue and brightness, and chroma if necessary, and R, G and B which are used in a television system or C, M, Y and K which are basic printing colors in a computer system are normally used. Based on the color data of the individual areas and a previously set foundation program, foundations to be applied on the individual areas are determined. Finally, the thud determined foundations are applied on the face of the subject person in accordance with the segmented areas.

One makeup simulation method according to the present invention and a makeup method using this simulation method therefore include the following steps: (a) determining a desirable face and performing image processing on an image of a face of a subject person based on the desirable face, thereby forming images of imagined post-makeup faces; (b) displaying the imagined post-makeup faces, prepared in the step (a), on a monitor screen or the like and selectively determining an ideal post-makeup face desired by the subject person from the displayed imagined post-makeup faces; (c) deriving a makeup procedure from an image of the ideal post-makeup face, determined in the step (b), based on a previously set makeup program: and (d) applying makeup on the face of the subject person in accordance with the makeup procedure derived in the step (c).

Another makeup simulation method embodying the present invention and another makeup method using this simulation method, particularly, a makeup simulation method for applying makeup based on dark and bright states on a face and a makeup method using this simulation method, include the following steps: (e) determining a desirable face and performing image processing on an image of a face of a subject person based on the desirable face, thereby forming images of imagined post-makeup faces; (f) displaying the imagined post-makeup faces, prepared in the step (e), on a monitor screen or the like and selectively determining an ideal post-makeup face desired by the subject person from the displayed imagined post-makeup faces; (g) performing image processing to segment an image of the ideal post-makeup face, determined in the step (f), to a plurality of areas in regard to bright areas and dark areas; (h) acquiring color data for the segmented areas obtained in the step (g); (i) determining foundations to be applied on individual areas based on the color data for those areas, acquired in the step (h), and a previously set foundation program; and (j) separately applying foundations, determined in the step (i), on the face of the subject person in association with the individual areas.

The makeup method based on dark and bright states may be modified in such a way as to be able to print the image of the ideal post-makeup face, segmented into a plurality of areas in regard to bright areas and dark areas in the step (g), in an actual size of the face of the subject person, to cut out individual areas from the printed image to prepare a pattern mask for foundation, and to execute separate application of foundations in the step (k) by using this pattern mask. This design can allow different foundations to be separately applied on the associated areas easily and accurately. That is, separate application of different foundations associated with an ideal post-makeup face can be carried out easily and accurately.

The makeup method which is based on the highlight theory may be modified in such a manner as to be able to project the image of the ideal post-makeup face, segmented into a plurality of areas in regard to bright areas and dark areas in the step (g), in an actual size on the face of the subject person, and to execute separate application of foundations in the step (j) based on this projected image. This modification can also permit different foundations to be separately applied on the associated areas easily and accurately.

Another makeup method according to the present invention which is based on dark and bright states includes the following steps: (A) determining a desirable face and performing image processing on an image of a face of a subject person based on the desirable face, thereby forming images of imagined post-makeup faces; (B) displaying the imagined post-makeup faces, prepared in the step (A), on a monitor screen or the like and selectively determining from the displayed imagined post-makeup faces an ideal post-makeup face the subject person desires; (C) performing image processing to segment an image of the ideal post-makeup face, determined in the step (B), to a plurality of areas in regard to bright areas and dark areas; (D) acquiring color data for the segmented areas obtained in the step (C); (E) determining foundations to be applied on individual areas based on the color data for those areas, acquired in the step (D), and a previously set foundation program; (F) printing foundations, determined in the step (E) in association with the plurality of areas segmented in regard to bright areas and dark areas in the image processing in the step (C), on a thin base material to prepare a transfer film; and (G) transferring foundations, printed on the transfer film prepared in the step (F), on the face of the subject person to thereby apply foundations, associated with the individual areas, on the face of the subject person.

A further makeup method according to the present invention which is based on dark and bright states includes the following steps: (H) determining a desirable face and performing image processing on an image of a face of a subject person based on the desirable face, thereby forming images of imagined post-makeup faces; (I) displaying the imagined post-makeup faces, prepared in the step (H), on a monitor screen or the like and selectively determining from the displayed imagined post-makeup faces an ideal post-makeup face the subject person desires; (K) printing an image of the ideal post-makeup face in the bright and dark states, determined in the step (I), on a thin base material using foundations to prepare a foundation transfer film; and (L) transferring foundations, printed on the foundation transfer film prepared in the step (K), on the face of the subject person to thereby apply the foundations on the face of the subject person.

Those methods can repeatedly realize makeup for an ideal post-makeup face by carrying out simple procedures, such as transferring foundations from a transfer film accurately corresponding to foundations for the ideal post-makeup face and properly shading off the transferred foundations at the boundaries between the individual areas. Thus, desired makeup can be carried out more easily and in a shorter time.

A makeup support apparatus according to the present invention for use in the foregoing makeup simulation methods and makeup methods comprises image storage means for storing images of a plurality of model faces; imaging and input means for imaging and inputting a face of a subject person; a monitor for displaying a necessary image; and processing means capable of performing a process of causing an image of the face of the subject person to approach a desirable face already determined to thereby form images of imagined post-makeup faces, a process of displaying the imagined post-makeup faces on a screen of the monitor, and a process of deriving a makeup procedure from a determined ideal post-makeup face.

It is preferable that the processing means in the makeup support apparatus may further perform a process of segmenting the determined ideal post-makeup face to a plurality of areas in regard to bright areas and dark areas, a process of acquiring color data for the segmented areas, and a process of determining foundations to be applied on individual areas based on the acquired color data for those areas.

BEST MODE FOR CARRYING OUT THE INVENTION

Hereinbelow, carrying-out modes of the present invention will described. To begin with, a carrying-out mode of a facial image modifying method according to the present invention will be described. Normally, a system which includes a data processing apparatus like a personal computer and a monitor connected to the apparatus is used in implementing the facial image modifying method of the present invention. An image of a face to be modified or an original facial image is put into the data processing apparatus. Then, a desirable face is selected from previously prepared model faces, e.g., multiple standard faces which have been prepared based on the average theory, and the original facial image is subjected to image processing based on this desirable face.

Figure 1:
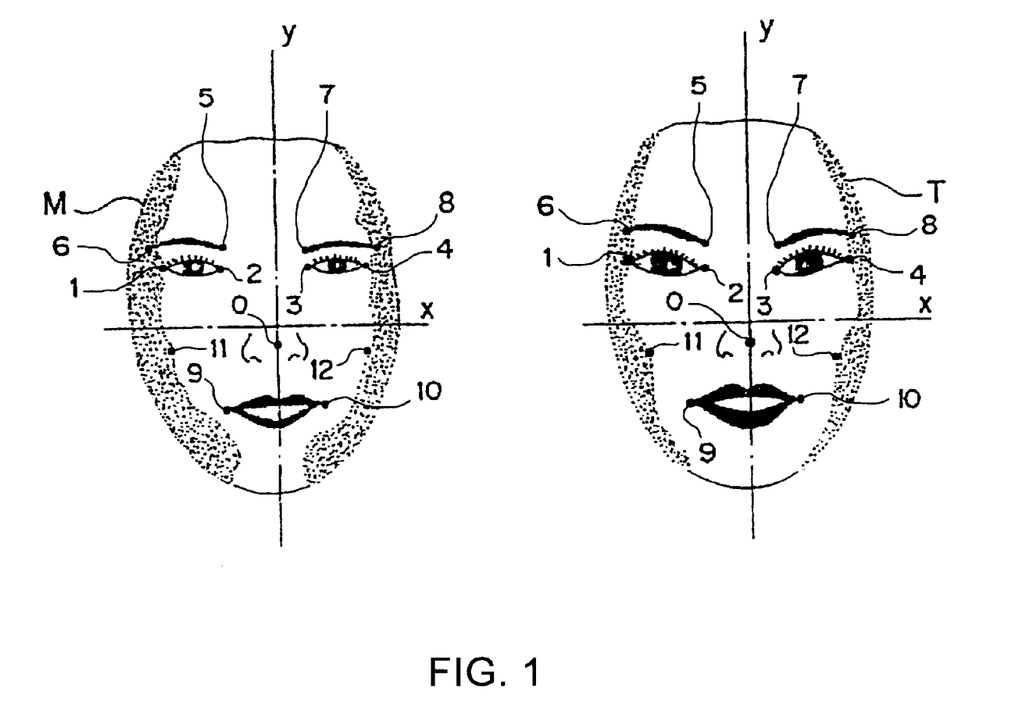
FIG. 1 is a diagram for explaining one example of image processing in a facial image modifying method.

The image processing is executed by a program which employs an image processing scheme like morphing or twining. Specifically, the coordinate values of facial constituents, such as eyebrows, eyes, a nose and a mouth, of both an original facial image M and a desirable face T, and the coordinate values of bright and dark patterns of each face are acquired as shown in FIG. 1, for example, and the original facial image M is mixed with and transformed toward the desirable face T based on those coordinate values.

More specifically, first, essential portions, such as eyebrows, eyes, a nose, a mouth and the lines of highlighted areas, are plotted for each of the original facial image M and the desirable face T. For example, a tip portion of the nose is expressed as "0", the eye lines as "1-2" and "3-4", and the eyebrows as "5-6" and "7-8". Then, those points on the original facial image M are shifted toward the corresponding points on the desirable face T by a morphing program. The lines of the highlighted areas or the like are shifted or their inclinations are changed by a twining program. Such image processing by shifting points or the like includes a plurality of phases according to the degree of such shifting. That is, selectable modified faces (imagined post-makeup faces in the case of a makeup method which will be described later) corresponding to those phases can be obtained. If point shifting is performed every one tenth of the distance between corresponding points on both facial images, for example, there are ten phases and there are thus ten imagined post-makeup faces. According to the experiments conducted by the present inventor, most of the times, subject persons found their "ideal faces" (selectable modified faces or imagined post-makeup faces) on selectable modified faces at the second or third phase, i.e., selectable modified faces which had approached to their desirable faces by degrees of 20 to 30%. That is, while there is a desirable face as an image, a face too close to this desirable face comes off the actual "ideal face".

As the above process forms the images of a plurality of selectable modified faces with different similarity levels with respect to a desirable face, they are displayed on the screen of the monitor to permit the subject person to make the best selection, which is treated as a modified facial image.

Figure 2:
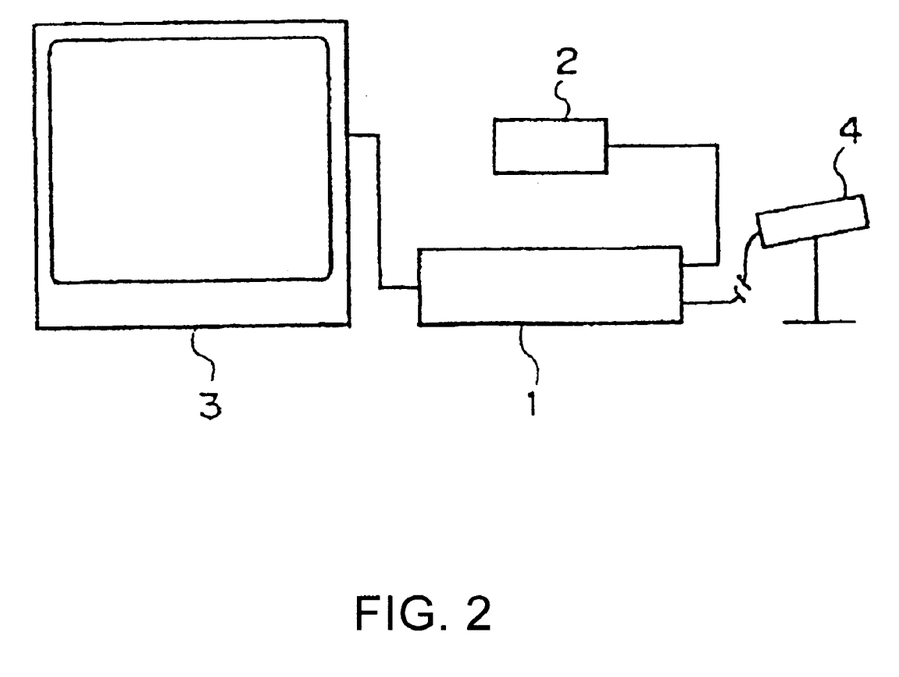
FIG. 2 is a structural diagram of a makeup support apparatus according to one carrying-out mode of the present invention.

Now, carrying-out modes of a makeup simulation method and a makeup method according to the present invention will be described. The makeup method of the present invention is carried out by using a makeup support apparatus. The makeup support apparatus of which structure is illustrated in FIG. 2 includes a data processing apparatus 1, a storage device 2, a monitor 3 and an image sensing unit 4.

The data processing apparatus 1, which executes various kinds of data processing required in the makeup method of the present invention, is a personal computer or the like. The storage device 2 is used to store data of model faces which are used in the makeup method of the present invention. An internal memory device or an external memory device is used as the storage device 2.

In an exemplified case where a makeup instructor instructs a subject person a makeup procedure using such a makeup support system, the makeup method proceeds as follows. First, the instructor asks the subject person specific questions to determine the impression of a face desired by the subject person or a desirable face. Model faces are used to make a desirable face concrete. As model faces are used image data of faces of popular talents, actresses or actors or the like, or standard good-looking faces prepared in association with human races or the like, which are stored in the storage device 2. A desirable face is selected from the model faces by using an average face for each race, each era, each personality, each work or the like or the name of a specific talent, or is selected from various model faces sequentially displayed on the screen of the monitor 3.

Once the desirable face is determined, the face of the subject person is picked up by the image sensing unit 4 and its image is sent into the storage device 2. By performing image processing on the image of the face of the subject person using the data processing apparatus 1, the image of the face of the subject person and the image of the desirable face are mixed to make the former image closer to the latter. In the image processing, the original facial image of the face of the subject person acquired in the above process is subjected to the same scheme as employed in the above-described modifying method to make the highlighted areas, the shapes of the eyebrows, the eye lines. the lip line and the like on the face approach those of the desirable face step by step.

Figure 3A:
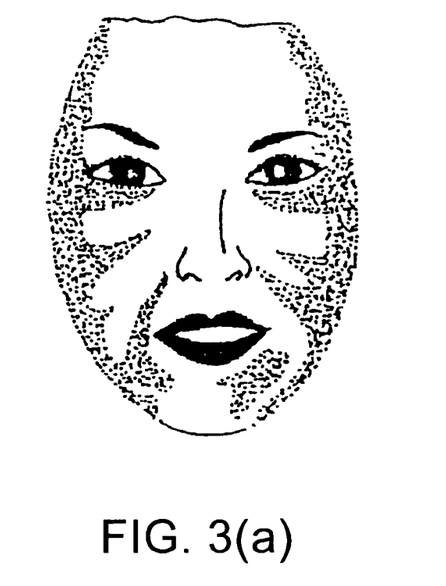
FIG. 3 is an explanatory diagram concerning a highlight theory.
Figure 3B:
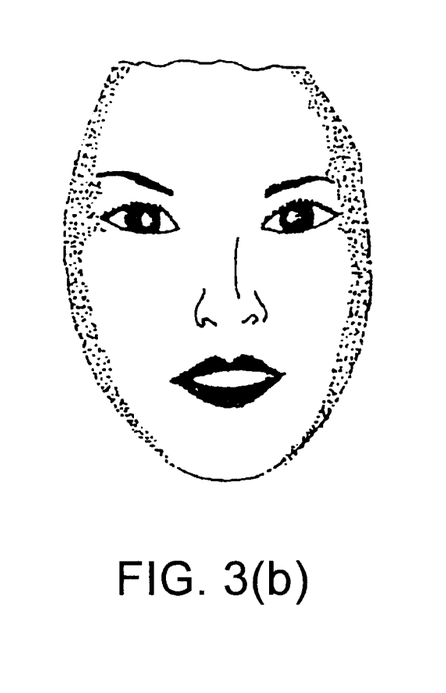

FIG. 3 exemplifies highlighted areas. (a) in FIG. 3 shows the states of bright and dark areas on the original facial image of the face of the subject person, and (b) in FIG. 3 shows the states of bright and dark areas made close to those of the desirable face in image processing. In the figure, the densely dotted portions represent relatively dark portions or dark areas and a portion surrounded by the dark portions represent the brightest area (highlighted area). As apparent from this example in which the highlighted area belongs to an oval shape, the current face of the subject person is off the ideal oval shape and the face of the subject person can be made closer to the desirable face which has an ideal oval highlighted area by mainly modifying the off portions.

As this process proceeds, the images of a plurality of imagined post-makeup faces with different similarity levels with respect to a desirable face are formed as described above, and those images are displayed on the screen of the monitor 3 to permit the subject person to make a selection. If the subject person agrees with any of the displayed images, the selected face is set as an ideal post-makeup face.

Once the ideal post-makeup face is determined, a sequence of makeup procedures about portions of eyebrows to be shaved and where to draw eyebrows, the lines and ranges for eye liners and eye shadows, the drawing range for a lipstick and separate application of different foundations, is derived from the ideal post-makeup face. This sequence is carried out by a previously set makeup program.

Figure 4:
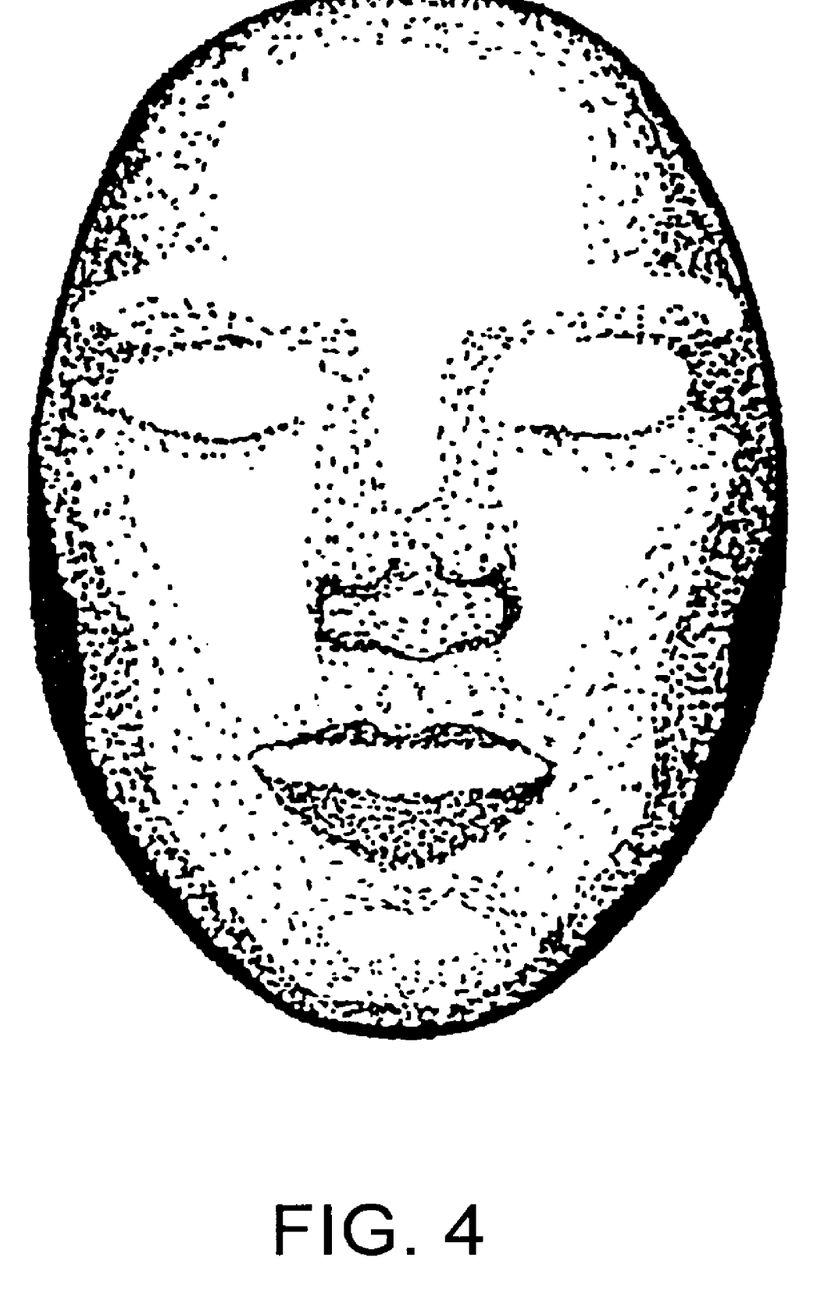
FIG. 4 is a diagram for explaining segmentation into highlighted areas.
Figure 5A:
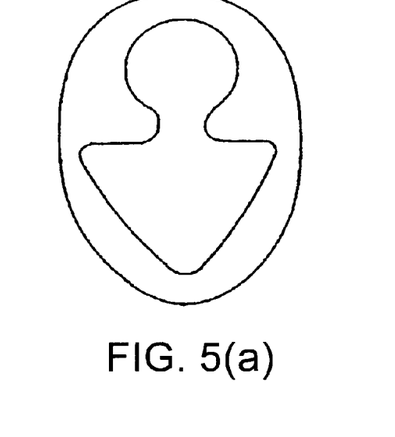
FIG. 5 is an explanatory diagram of the types of highlighted areas.
Figure 5B:
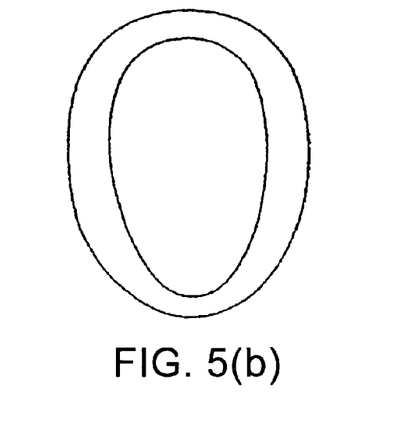
Figure 5C:
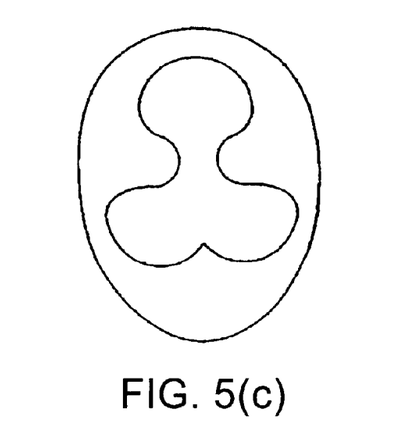

With regard to foundation, in particular, how to apply foundations is derived by performing the following processes under the control of a foundation program which is included in the makeup program. First, image processing is performed to divide the ideal post-makeup face into a plurality of bright and dark areas, e.g., two to four areas. This process is exemplified in FIG. 4. In the exemplified diagram, the face is segmented to four areas with different brightnesses (black-filled portion, densely-dotted portion, thinly-dotted portion and white portion). Next, color data for the segmented areas are acquired. The color data in this case are based on R, G and B used in a television system. Based on the obtained color data of each area, a foundation to be applied on that area is determined.

As the makeup procedure needed for making up the face of the subject person into the ideal post-makeup face and cosmetics to be used in the makeup procedure are determined in the above manner, actual makeup is finally applied to the face of the subject person based on what has been determined. In utilizing the thus derived makeup procedure and the like in the actual makeup, data about the makeup procedure, etc. should be displayed on the monitor screen or printed out.

According to a second carrying-out mode of the present invention, a pattern mask is used to apply foundations on the face of a subject person. A pattern mask is formed like a pattern sheet by cutting out individual areas from a printed image of the face, segmented into a plurality of areas in regard to bright areas and dark areas in the above-described image processing, in the real size of the face of the subject person. Then, the pattern mask is placed on the face of the subject person and foundations for the individual areas are applied over the pattern mask.

A third carrying-out mode of the present invention employs a projection scheme to apply foundations on the face of a subject person. Specifically, the image of the face, segmented into a plurality of areas in regard to bright areas and dark areas in the above-described image processing, is projected on the face of the subject person in real size, and foundations for the associated areas are separately applied based on this projected image.

A fourth carrying-out mode of the present invention uses a transfer scheme to apply foundations on the face of a subject person. Specifically, first, in association with a plurality of areas segmented in regard to bright areas and dark areas in the above-discussed image processing, foundations for the respective areas are printed in an actual size on a thin base material to prepare a foundation transfer film. Alternatively, images of bright and dark states on the ideal post-makeup face determined in the above-described manner are printed on a thin base material using foundations to prepare a foundation transfer film. Then, such a foundation transfer film is pressed against the face of the subject person to transfer the foundations. Finally, the proper shade-off process or the like is performed on the transferred foundations at the boundaries between the individual areas. The foundation transfer film in this case does not necessarily correspond to the entire face, but a partial transfer film for the upper eyelids or a portion around the nose, for example, may be used.

According to the fourth carrying-out mode of the present invention, application of foundations to the face of the subject person is accomplished by directly printing the foundations on the face by means of a three-dimensional printer or the like. Specifically, an image with separately applied foundations, which is formed by the above-described image processing, is directly spray-printed on the face by a three-dimensional printer or the like which uses the necessary foundations as inks.

What is claimed is:

1. A makeup simulation method comprising the steps of:
  (a) determining a desirable face and performing image processing to produce a plurality of images of imagined post-makeup faces with a different mixing ratio by mixing an image of said desirable face with an image of a face of a subject person;
  (b) displaying said plurality of images of imagined post-makeup faces, prepared in said step (a), on a monitor screen and selectively determining from said displayed imagined post-makeup faces an ideal post-makeup face said subject person desires; and
  (c) deriving a makeup procedure from an image of said ideal post-makeup face, determined in said step (b), based on a previously set makeup program.

2. A makeup simulation method or executing makeup simulation based on shading states of a face, comprising the steps of:
  (e) determining a desirable face and performing image processing on an image of a face of a subject person based on said desirable face, thereby forming images of imagined post-makeup faces;
  (f) displaying said imagined post-makeup faces, prepared in said step (e), on a monitor screen and selectively determining from said displayed imagined post-makeup faces an ideal post-makeup face said subject person desires;
  (g) performing image processing to segment an image of said ideal post-makeup face, determined in said step (f), to a plurality of areas in regard to bright areas and dark areas;
  (h) acquiring color data for said segmented areas obtained in said step (g); and
  (i) determining foundations to be applied on individual areas based on said color data for those areas, acquired in said step (h), and a previously set foundation program.

3. The makeup simulation method according to claim 2 further comprising a step of preparing a plurality of model faces and determining said desirable face based on said model faces.

4. A makeup method comprising the steps of:
  (a) determining a desirable face and performing image processing to produce a plurality of images of imagined post-makeup faces with a different mixing ratio by mixing an image of said desirable face with an image of a face of a subject person;
  (b) displaying said plurality of imagined post-makeup faces, prepared in said step (a), on a monitor screen and selectively determining from said displayed imagined post-makeup faces an ideal post-makeup face said subject person desires;
  (c) deriving a makeup procedure from an image of said ideal post-makeup face, determined in said step (b), based on a previously set makeup program; and
  (d) applying makeup on said face of said subject person in accordance with said makeup procedure derived in said step (c).

5. A makeup method for applying makeup based on shading states of a face, comprising the steps of:
  (e) determining a desirable face and performing image processing on an image of a face of a subject person based on said desirable face, thereby forming images of imagined post-makeup faces;
  (f) displaying said imagined post-makeup faces, prepared in said step (e), on a monitor screen and selectively determining from said displayed imagined post-makeup makeup faces an ideal post-makeup face said subject person desires;

(g) performing image processing to segment an image of said ideal post-makeup face, determined in said step (f), to a plurality of areas in regard to bright areas and dark areas;

(h) acquiring color data for said segmented areas obtained in said step (g);

(i) determining foundations to be applied on individual areas based on said color data for those areas, acquired in said step (h), and a previously set foundation program; and (j) separately applying foundations, determined in said step (i), on said face of said subject person in association with said individual areas.

6. The makeup method according to claim 5, further comprising:

(k) printing said image of said ideal post-makeup face, segmented into a plurality of areas in regard to bright areas and dark areas in said step (g) in claim 5, in an actual size of said face of said subject person;

(l) cutting individual areas from a printed image obtained in said step (k) to prepare a pattern mask for foundation; and (m) executing separate application of foundations in said step (j) in claim 5 using said pattern mask prepared in said step (l).

7. The makeup method according to claim 5, further comprising;

(n) projecting said image of said ideal post-makeup face, segmented into a plurality of areas in regard to bright areas and dark areas in the image processing in said step (g) in claim 6, in an actual size on said face of said subject person; and (o) executing separate application of foundations in said step (j) in claim 6 based on said image projected in said step (n).

8. A makeup method for applying makeup based on bright and dark states of a face, comprising the steps of:

(A) determining a desirable face and performing image processing on an image of a face of a subject person based on said desirable face, thereby forming images of imagined post-makeup faces;

(B) displaying said imagined post-makeup faces, prepared in said step (A), on a monitor screen and selectively determining from said displayed imagined post-makeup faces an ideal post-makeup face said subject person desires;

(C) performing image processing to segment an image of said ideal post-makeup face, determined in said step (B), to a plurality of areas in regard to bright areas and dark areas;

(D) acquiring color data for said segmented areas obtained in said step (C);

(E) determining foundations to be applied on individual areas based on said color data for those areas, acquired in said step (D), and a previously set foundation program;

(F) printing foundations, determined in said step (E) in association with said plurality of areas segmented in regard to bright areas and dark areas in said image processing in said step (C), on a thin base material to prepare a foundation transfer film; and (G) transferring foundations, printed on said foundation transfer film prepared in said step (F), on said face of said subject person to thereby apply foundations, associated with said individual areas on said face of said subject person.

9. A makeup method comprising the steps of:

(H) determining a desirable face and performing image processing on an image of a face of a subject person based on said desirable face, thereby forming images of imagined post-makeup faces;

(I) displaying said imagined post-makeup faces, prepared in said step (H), on a monitor screen and selectively determining an ideal post-makeup face desired by said subject person from said displayed imagined post-makeup faces;

(K) printing an image of said ideal post-makeup face, determined in said step (I), on a thin base material using foundations to prepare a foundation transfer film; and (L) transferring foundations, printed on said foundation transfer film prepared in said step (K), on said face of said subject person to thereby apply said foundations on said face of said subject person.

10. The makeup method according to any one of claim 4 further comprising a step of preparing a plurality of model faces and determining said desirable face based on said model faces.

11. A makeup support apparatus for use in the makeup simulation method as recited in claim 1, comprising:

image storage means for storing images of a plurality of model faces;

image pick-up and input means for imaging and inputting a face of a subject person;

a monitor for displaying a necessary image; and processing means capable of performing a process of causing an image of said face of said subject person to approach a desirable face already determined to thereby form images of imagined post-makeup faces, a process of displaying said imagined post-makeup faces on a screen of said monitor, and a process of deriving a makeup procedure from a determined ideal post-makeup face.

12. The makeup support apparatus according to claim 11, wherein said processing means further performs a process of segmenting said determined ideal post-makeup face to a plurality of areas in regard to bright areas and dark areas, a process of acquiring color data for said segmented areas, and a process of determining foundations to be applied on individual areas based on said acquired color data for those areas.

13. The makeup simulation method according to claim 2, further comprising a step of preparing a plurality of model faces and determining said desirable face based on said model faces.

14. A makeup support apparatus for use in the makeup simulation method as recited in claim 4, comprising:

image storage means for storing images of a plurality of model faces;

image pick-up and input means for imaging and inputting a face of a subject person;

a monitor for displaying a necessary image; and processing means capable of performing a process of causing an image of said face of said subject person to approach a desirable face already determined to thereby form images of imagined post-makeup faces, a process of displaying said imagined post-makeup faces on a screen of said monitor, and a process of deriving a makeup procedure from a determined ideal post make-up.

15. A makeup support apparatus for use in the makeup simulation method as recited in claim 8, comprising:

image storage means for storing images of a plurality of model faces;

image pick-up and input means for imaging and inputting a face of a subject person;

a monitor for displaying a necessary image; and processing means capable of performing a process of causing an image of said face of said subject person to approach a desirable face already determined to thereby form images of imagined post-makeup faces, a process of displaying said imagined post-makeup faces on a screen of said monitor, and a process of deriving a makeup procedure from a determined ideal post make-up.

* * * * *